United States Patent
Murugan et al.

(10) Patent No.: US 10,745,348 B2
(45) Date of Patent: Aug. 18, 2020

(54) PROCESS FOR MAKING DIARYL SULFONES

(71) Applicant: Vertellus Holdings LLC, Indianapolis, IN (US)

(72) Inventors: Ramiah Murugan, Indianapolis, IN (US); David A. Hay, Indianapolis, IN (US)

(73) Assignee: Vertellus Holdings LLC, Indianapolis, IN (US)

( * ) Notice: Subject to any disclaimer, the term of this patent is extended or adjusted under 35 U.S.C. 154(b) by 0 days.

(21) Appl. No.: 15/580,486

(22) PCT Filed: Jun. 9, 2016

(86) PCT No.: PCT/US2016/036587
§ 371 (c)(1),
(2) Date: Dec. 7, 2017

(87) PCT Pub. No.: WO2016/201039
PCT Pub. Date: Dec. 15, 2016

(65) Prior Publication Data
US 2018/0179153 A1    Jun. 28, 2018

Related U.S. Application Data

(60) Provisional application No. 62/173,283, filed on Jun. 9, 2015.

(51) Int. Cl.
| | |
|---|---|
| *C07C 315/00* | (2006.01) |
| *C07C 303/06* | (2006.01) |
| *B01J 23/745* | (2006.01) |
| *B01J 21/02* | (2006.01) |
| *B01J 21/06* | (2006.01) |
| *B01J 23/06* | (2006.01) |
| *B01J 23/18* | (2006.01) |
| *B01J 31/02* | (2006.01) |

(52) U.S. Cl.
CPC ............. *C07C 315/00* (2013.01); *B01J 21/02* (2013.01); *B01J 21/066* (2013.01); *B01J 23/06* (2013.01); *B01J 23/18* (2013.01); *B01J 23/745* (2013.01); *B01J 31/0215* (2013.01); *B01J 31/0258* (2013.01); *C07C 303/06* (2013.01)

(58) Field of Classification Search
CPC . B01J 21/02; B01J 21/066; B01J 23/06; B01J 23/18; B01J 31/0215; B01J 31/0258; C07C 315/00
See application file for complete search history.

(56) References Cited

U.S. PATENT DOCUMENTS

| | | | |
|---|---|---|---|
| 2,971,985 A | 2/1961 | Joly et al. | |
| 3,309,409 A | 3/1967 | Steiger | |
| 3,355,497 A | 11/1967 | Budnick | |
| 3,855,312 A | 12/1974 | Horner | |
| 4,012,451 A | 3/1977 | Enoki et al. | |
| 4,778,932 A | 10/1988 | Manami et al. | |
| 4,822,916 A * | 4/1989 | Aaronson | C07C 315/00 568/34 |
| 4,871,876 A | 10/1989 | Schaefer et al. | |
| 4,876,390 A | 10/1989 | McCulloch | |
| 4,937,387 A | 6/1990 | Steiner et al. | |
| 4,983,773 A | 1/1991 | Stumpp et al. | |
| 5,082,973 A | 1/1992 | Stumpp et al. | |
| 9,340,496 B2 * | 5/2016 | Bandodkar | C07C 315/00 |
| 2011/0263902 A1 | 10/2011 | Deck et al. | |
| 2011/0263903 A1 | 10/2011 | Deck et al. | |
| 2012/0302795 A1 | 11/2012 | Bandokar et al. | |
| 2014/0039222 A1 * | 2/2014 | Louis | C07C 315/00 568/34 |
| 2014/0364659 A1 | 12/2014 | Bandokar et al. | |

FOREIGN PATENT DOCUMENTS

| | | | | |
|---|---|---|---|---|
| CH | 497396 A | | 10/1970 | |
| CN | 1623982 A1 | | 6/2005 | |
| CN | 102351759 A | | 2/2012 | |
| DE | 3704932 A1 | | 9/1988 | |
| EP | 0381045 A2 | | 8/1990 | |
| EP | 0455332 | | 11/1991 | |
| EP | 2383256 A1 | | 11/2011 | |
| EP | 2383257 A1 | | 11/2011 | |
| GB | 895464 | * | 5/1962 | |
| JP | 51082237 A | | 7/1976 | |
| JP | s5785363 | | 5/1982 | |
| JP | 06116231 | * | 4/1994 | ........... C07C 317/14 |
| JP | 06116231 A1 | | 4/1994 | |
| JP | 9143150 A | | 6/1997 | |
| JP | 09157246 A1 | | 6/1997 | |

(Continued)

OTHER PUBLICATIONS

PCT Search Report and Written Opinion for PCT/US2016/036587, completed Sep. 8, 2016.
Farberov, M. I.; et al., "Technical synthesis of 4,4'-dichlorodiphenylsulfone based on chlorobenzene, sulfur trioxide, and dimethyl sulfate," Khimicheskaya Promyshlennost (Moscow, Russian Federation), 1972, 48, 585-587, abstract only.
Andrashchuk, N. et al., "Reaction of methyl methanesulfonate with sulfur trioxide and chlorobenzene," Zhumal Organicheskoi Khimii, 1987, 23, 1264-8, abstract only.

(Continued)

*Primary Examiner* — Rosalynd A Keys

(74) *Attorney, Agent, or Firm* — Barnes & Thornburg, LLP

(57) ABSTRACT

A process for preparing diaryl sulfones, such as 4,4'-dichlorodiphenylsulfone is disclosed. The process comprises contacting an aryl compound with sulfur trioxide to provide a benzene sulfonic acid. The benzene sulfonic acid is coupled to additional aryl compound in the presence of a catalyst. During the coupling step, the additional aryl compound is continuously added while water is removed.

26 Claims, 1 Drawing Sheet

(56) References Cited

FOREIGN PATENT DOCUMENTS

| JP | 9165366 A | 6/1997 |
|---|---|---|
| JP | 09188663 A1 | 7/1997 |
| JP | H10017542 | 1/1998 |
| RO | 113981 B1 | 12/1998 |
| WO | WO2011107465 | 9/2011 |
| WO | 2013087594 | 6/2013 |

OTHER PUBLICATIONS

Velluz, L. et al., "Dimethyl pyrosulfate in the preparation of diaryl sulfones," Compt. rend., 1959, 248, 114-115, abstract only.

Olah, G. A., et al., "Nafion-H catalysed sulfonylation of aromatics with arene/alkenesulfonic acids for the preparation of sulfones," Chemical Communications, 2001, 17, 1696-1697.

Hajipour, A. R., et al., "Direct sulfonylation of aromatic rings with aryl or alkyl sulfonic acid using supported P2O5/Al2O3," Phosphorous, Sulfur and Silicon and the Related Elements, 2005, 180, 2029-2034.

Sharghi, H. et al., "Al2O3/MeSO3H (AMA) a Useful System for Direct Sulfonylatoin of Phenols with p-Toluenesulfonic Acid," Journal of the Iranian Chemical Society, 2005, 2(1), 47-53.

Ueda, M. et al., "A New Synthesis of Diaryl Sulfones," Synthesis, 1984, (4), 323-5.

\* cited by examiner

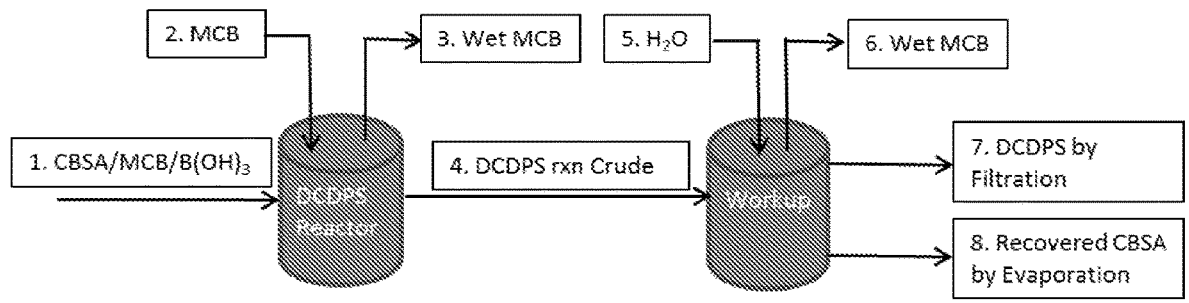

PROCESS FOR MAKING DIARYL SULFONES

CROSS REFERENCE TO RELATED APPLICATIONS

This application is a national stage entry made under 35 U.S.C. § 371(b) of PCT International Application No. PCT/US2016/036587, filed Jun. 9, 2016, which claims priority under 35 U.S.C. § 119(e) to U.S. Provisional Application Ser. No. 62/173,283, filed Jun. 9, 2015, each of which is incorporated herein by reference in its entirety.

FIELD OF THE INVENTION

The invention described herein pertains to a process for making diaryl sulfones, such as 4,4'-dihalodiphenyl sulfones.

BACKGROUND OF THE INVENTION

Several processes for preparing diaryl sulfones, such as 4,4'-dichlorodiphenylsulfone (DCDPS) are known. Such processes may utilize various paths to make diaryl sulfones starting various aryl starting materials, such as from chlorobenzene.

In one exemplary diaryl sulfone preparation described in U.S. Pat. No. 4,937,387, DCDPS is produced from sulfur trioxide and monochlorobenzene in a two-step process. The first step is the reaction of monochlorobenzene with sulfur trioxide to form chlorobenzene sulfonic acid (CBSA). The second step is the reaction of chlorobenzene sulfonic acid with monochlorobenzene. The reaction in reported to result in an average conversion to DCDPS of 20.8% based on CBSA and sulfuric acid feed (Table I). Additional steps are taken to recover unreacted CBSA for repeating the second step to form additional DCDPS.

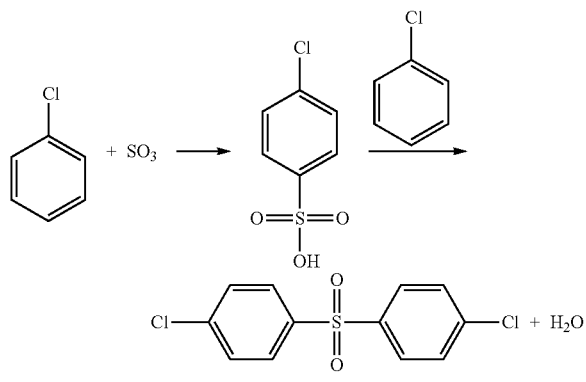

U.S. Pat. No. 4,937,387 DCDPS Process

In another exemplary diaryl sulfone preparation described in U.S. Pat. No. 4,983,773, DCDPS is formed from chlorobenzene and sulfonic acid with added boric acid in a one-step process. Purification is performed by selective washing with a solvent, by fractional crystallization or by centrifuging. The reported yield is 84%

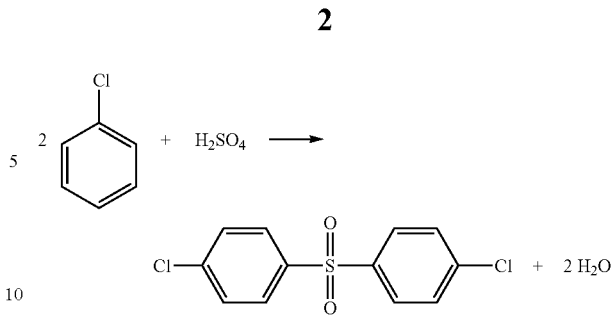

U.S. Pat. No. 4,983,773 DCDPS Process

In yet another exemplary diaryl sulfone preparation described in WO Patent Publication No. WO 2012/143281, DCDPS is formed from chlorobenzene, sulfuric acid, and trifluoroacetic anhydride (TFAA) as a dehydrating reagent. The overall reaction does not result in water as a product because TFAA is converted to trifluoroacetic acid (TFA). The best reported yield is 100%. However, this process uses stoichiometric amounts of TFAA.

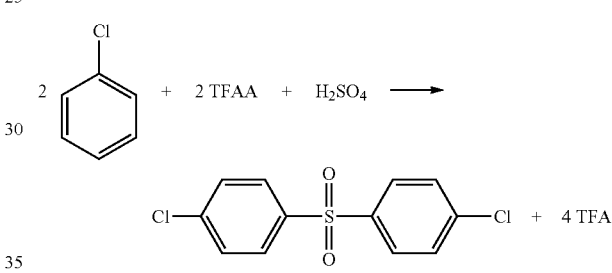

WO 2012/143281 DCDPS Process

There remains a needs for a more economical process for producing diaryl sulfones, such as 4,4'-dichlorodiphenylsulfone. Specifically, there remains a need for a process for efficiently producing diaryl sulfones, such as DCDPS, in high yield and high selectivity with minimal byproduct formation.

SUMMARY OF THE INVENTION

In some embodiments, the disclosure provides a process for preparing a sulfone of the formula

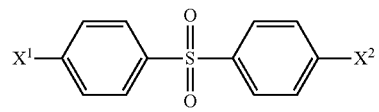

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl; the process comprising a. a coupling step comprising contacting a sulfonic acid of the formula

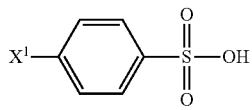

with an aryl compound of the formula

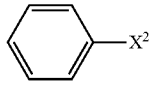

in the presence of a catalyst, wherein resulting water is removed during the coupling step.

In some embodiments, the disclosure provides a process for preparing a sulfone of the formula

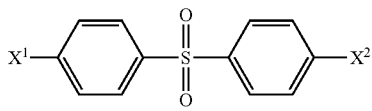

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl; the process comprising a. a first step contacting an aryl reactant of the formula

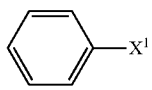

with sulfur trioxide to provide a first product mixture comprising a sulfonic acid of the formula

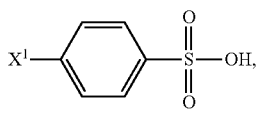

and b. a coupling step comprising contacting the sulfonic acid of the formula

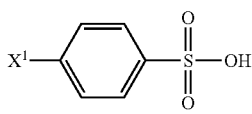

with an aryl halide of the formula

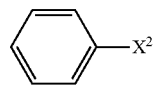

in the presence of a catalyst, wherein resulting water is removed during the coupling step.

In some embodiments, the disclosure provides a process for preparing a sulfone of the formula

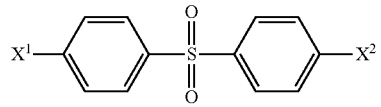

wherein $X^1$ and $X^2$ are independently halogens, the process comprising a coupling step comprising contacting a sulfonic acid with an aryl halide in the presence of a catalyst, wherein resulting water is removed during the coupling step.

In some embodiments, the disclosure provides a process for preparing a sulfone of the formula

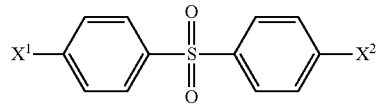

wherein $X^1$ and $X^2$ are independently halogens, the process comprising a first step comprising contacting an aryl halide reactant with sulfur trioxide to provide a first product mixture comprising a sulfonic acid, and a coupling step comprising contacting the sulfonic acid with an aryl halide in the presence of a catalyst, wherein resulting water is removed during the coupling step.

Embodiments of the invention are further described by the following enumerated clauses. It will be understood that any of the embodiments described herein can be used in connection with any other embodiments described herein to the extent that the embodiments do not contradict one another:

1. A process for preparing a sulfone of the formula

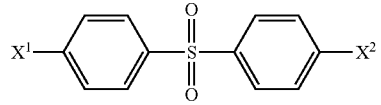

wherein $X^1$ and $X^2$ are independently halogens, the process comprising:

a coupling step comprising contacting a sulfonic acid of the formula

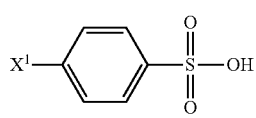

wherein $X^1$ is a halogen, with an aryl halide of the formula

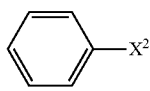

wherein $X^2$ is a halogen, in the presence of a catalyst, wherein resulting water is removed during the coupling step.

1a. A process for preparing a sulfone of the formula

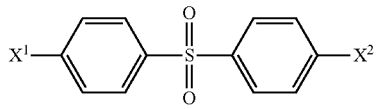

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl; the process comprising a. a coupling step comprising contacting a sulfonic acid of the formula

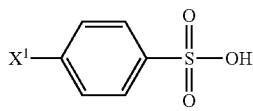

with an aryl compound of the formula

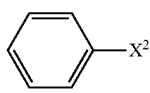

in the presence of a catalyst, wherein resulting water is removed during the coupling step.

2. The process of any of the preceding clauses, wherein $X^1$ and $X^2$ are Cl.

3. The process of any of the preceding clauses, wherein the crude yield of the coupling step, as determined by the sulfone relative to the sulfonic acid, is about 50% to about 100%, about 55% to about 100%, about 60% to about 100%, about 65% to about 100%, about 70% to about 100%, about 75% to about 100%, about 80% to about 100%, about 85% to about 100%, about 50% to about 95%, about 55% to about 95%, about 60% to about 95%, about 65% to about 95%, about 70% to about 95%, about 75% to about 95%, about 80% to about 95%, about 85% to about 95%, about 50% to about 90%, about 55% to about 90%, about 60% to about 90%, about 65% to about 90%, about 70% to about 90%, about 75% to about 90%, about 80% to about 90%, or about 85% to about 90%.

4. The process of any of the preceding clauses, wherein the crude yield of the coupling step, as determined by the sulfone relative to the sulfonic acid, is about 60% to about 95%.

5. The process of any of the preceding clauses, wherein the crude yield of the coupling step, as determined by the sulfone relative to the sulfonic acid, is about 82% to about 93%.

6. The process of any of the preceding clauses, wherein the purified yield of the coupling step, as determined by the sulfone relative to the sulfonic acid, is about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, 40% to about 90%, about 45% to about 90%, about 50% to about 90%, about 55% to about 90%, about 60% to about 90%, about 65% to about 90%, about 70% to about 90%, about 75% to about 90%, about 80% to about 90%, 40% to about 85%, about 45% to about 85%, about 50% to about 85%, about 55% to about 85%, about 60% to about 85%, about 65% to about 85%, about 70% to about 85%, about 75% to about 85%, or about 80% to about 85%.

7. The process of any of the preceding clauses, wherein the purified yield of the coupling step, as determined by the sulfone relative to the sulfonic acid, is about 50% to about 85%.

8. The process of any of the preceding clauses, wherein the purified yield of the coupling step, as determined by the sulfone relative to the sulfonic acid, is about 70% to about 75%.

9. The process of any of the preceding clauses, wherein the coupling step is initiated under anhydrous conditions.

10. The process of any of the preceding clauses, wherein the coupling step is initiated with less than about 10 wt % water, less than about 5 wt % water, less than about 1 wt % water, or less than about 0.5 wt % water.

11. The process of any of the preceding clauses, wherein the coupling step is initiated with less than about 10 wt % water.

12. The process of any of the preceding clauses, wherein the resulting water is removed continuously during the coupling step.

13. The process of any of the preceding clauses, wherein the resulting water is removed by distillation.

14. The process of any of the preceding clauses, wherein the concentration of water throughout the coupling step is less than about 10 wt % water, less than about 5 wt % water, less than about 1 wt % water, or less than about 0.5 wt % water.

15. The process of any of the preceding clauses, wherein the concentration of water throughout the coupling step is less than about 10 wt % water. 16. The process of any of the preceding clauses, wherein the coupling step is performed without a dehydrating reagent.

17. The process of any of the preceding clauses, wherein the concentration of the catalyst relative to all components of the coupling step, when the coupling step is initiated, is about 0.1 wt % to about 10 wt %, about 0.1 wt % to about 5 wt %, about 0.5 wt % to about 2 wt %, about 0.7 wt % to about 1.1 wt %, or about 0.9 wt %.

18. The process of any of the preceding clauses, wherein the concentration of the catalyst relative to all components of the coupling step, when the coupling step is initiated, is about 0.1 wt % to about 5 wt %.

19. The process of any of the preceding clauses, wherein the concentration of the catalyst relative to all components of the coupling step, when the coupling step is initiated, is about 0.7 wt % to about 1.1 wt %.

20. The process of any of the preceding clauses, wherein the amount of the catalyst relative to the sulfonic acid, when the coupling step is initiated, is about 0.01 equivalent to about 1 equivalent, about 0.01 equivalent to about 0.5 equivalent, about 0.01 equivalent to about 0.1 equivalent, about 0.01 to about 0.075 equivalent, about 0.02 equivalent to about 1 equivalent, about 0.02 equivalent to about 0.5 equivalent, about 0.02 equivalent to about 0.1 equivalent, about 0.02 to about 0.075 equivalent, about 0.025 equivalent, or about 0.05 equivalent.

21. The process of any of the preceding clauses, wherein the concentration of the catalyst relative to the sulfonic acid, when the coupling step is initiated, is about 0.01 equivalent to about 0.1 equivalent.

22. The process of any of the preceding clauses, wherein the concentration of the catalyst relative to the sulfonic acid, when the coupling step is initiated, is about 0.025 equivalent to about 0.05 equivalent.

23. The process of any of the preceding clauses, wherein the catalyst is selected from the group consisting of a boron catalyst, an iron catalyst, a zinc catalyst, a tin catalyst, a titanium catalyst, a zirconium catalyst, a bismuth catalyst, an antimony catalyst, a silica catalyst, a metal sulfate catalyst, a metal oxide catalyst, a sulfonic acid catalyst, an iodine catalyst, or a combination thereof.

24. The process of any of the preceding clauses, wherein the catalyst is selected from the group consisting of aluminum oxide, antimony oxide, zirconium oxide, bismuth oxide, boric anhydride, boric acid, ferric oxide, stannic oxide, titanium oxide, titanium sulfate, zinc oxide, iodine, lithium iodide, methane sulfonic acid, trifluoromethane sulfonic acid, silica and dimethylsulfate.

25a. The process of any of the preceding clauses, wherein the catalyst is aluminum oxide.

25b. The process of any of the preceding clauses, wherein the catalyst is zirconium oxide.

25c. The process of any of the preceding clauses, wherein the catalyst is bismuth oxide.

25d. The process of any of the preceding clauses, wherein the catalyst is boric anhydride.

25e. The process of any of the preceding clauses, wherein the catalyst is boric acid.

25f. The process of any of the preceding clauses, wherein the catalyst is ferric oxide.

25g. The process of any of the preceding clauses, wherein the catalyst is stannic oxide.

25h. The process of any of the preceding clauses, wherein the catalyst is titanium oxide.

25i. The process of any of the preceding clauses, wherein the catalyst is titanium sulfate.

25j. The process of any of the preceding clauses, wherein the catalyst is zinc oxide.

25k. The process of any of the preceding clauses, wherein the catalyst is iodine.

25l. The process of any of the preceding clauses, wherein the catalyst is lithium iodide.

25m. The process of any of the preceding clauses, wherein the catalyst is methane sulfonic acid.

25n. The process of any of the preceding clauses, wherein the catalyst is trifluoromethane sulfonic acid.

25o. The process of any of the preceding clauses, wherein the catalyst is silica.

25p. The process of any of the preceding clauses, wherein the catalyst is dimethylsulfate.

25q. The process of any of the preceding clauses, wherein the catalyst is antimony oxide.

26. The process of any of clauses 1 or 3-25, wherein the coupling step results in less than 20% of a 2,4' isomer of the formula

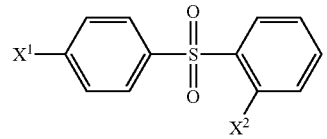

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 2,4' isomer relative to all sulfone products.

27. The process of any of clauses 1 or 3-26, wherein the coupling step results in less than 10% of a 2,4' isomer of the formula

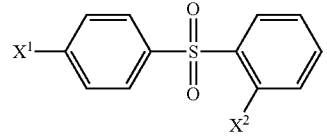

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 2,4' isomer relative to all sulfone products.

28. The process of any of clauses 1 or 3-27, wherein the coupling step results in less than 20% of a 3,4' isomer of the formula

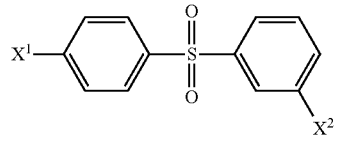

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 3,4' isomer relative to all sulfone products.

29. The process of any of clauses 1 or 3-28, wherein the coupling step results in less than 10% of a 3,4' isomer of the formula

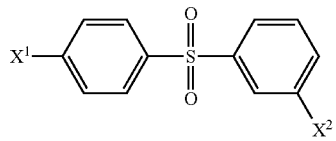

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 3,4' isomer relative to all sulfone products.

30. The process of any of clauses 26-29, wherein $X^1$ and $X^2$ are Cl.

31. The process of any of the preceding clauses, wherein the aryl halide or aryl compound is added to the sulfonic acid continuously during the coupling step.

32. The process of any of the preceding clauses, wherein the aryl halide or aryl compound is added to the sulfonic acid continuously for about 0.5 hour to about 20 hours, about 1 hour to about 20 hours, about 2 hours to about 20 hours, about 7 hours to about 20 hours, about 9 hours to about 20 hours, about 10 hours to about 20 hours, about 0.5 hour to about 15 hours, about 1 hour to about 15 hours, about 2 hours to about 15 hours, about 7 hours to about 15 hours, about 9 hours to about 15 hours, about 10 hours to about 15 hours, about 0.5 hour to about 13 hours, about 1 hour to about 13 hours, about 2 hours to about 13 hours, about 7 hours to about 13 hours, about 9 hours to about 13 hours, about 10 hours to about 13 hours, about 0.5 hour to about 12 hours, about 1 hour to about 12 hours, about 2 hours to about 12 hours, about 7 hours to about 12 hours, about 9 hours to about 12 hours, about 10 hours to about 12 hours, or about 10 hours.

33. The process of any of the preceding clauses, wherein the aryl halide or aryl compound is added to the sulfonic acid continuously for about 7 hours to about 13 hours.

34. The process of any of the preceding clauses, wherein the aryl halide or aryl compound is added to the sulfonic acid continuously for about 9 hours to about 12 hours.

35. The process of any of the preceding clauses, wherein the aryl halide or aryl compound is added to the sulfonic acid continuously for about 10 hours.

36. The process of any of the preceding clauses, wherein the aryl halide or aryl compound is added to the sulfonic acid continuously at the same time that water is removed continuously from the sulfonic acid.

37. The process of any of the preceding clauses, wherein the aryl halide or aryl compound is added to the sulfonic acid continuously at the same time that wet chlorobenzene is removed continuously from the sulfonic acid.

38. The process of any of the preceding clauses, wherein the aryl halide or aryl compound is added at a flow rate of about 0.1 mL/min to about 10 mL/min, about 0.5 mL/min to about 5 mL/min, about 0.5 mL/min to about 3 mL/min, or about 1.5 mL/min.

39. The process of any of the preceding clauses, wherein the aryl halide or aryl compound is added at a flow rate of about 1.5 mL/min.

40. The process of any of the preceding clauses, wherein the coupling step is performed at a coupling temperature of about 150° C. to about 280° C., about 160° C. to about 280° C., about 170° C. to about 280° C., about 180° C. to about 280° C., about 150° C. to about 260° C., about 160° C. to about 260° C., about 170° C. to about 260° C., about 180° C. to about 260° C., about 150° C. to about 240° C., about 160° C. to about 240° C., about 170° C. to about 240° C., or about 180° C. to about 240° C.

41. The process of any of the preceding clauses, wherein the coupling step is performed at a coupling temperature of about 180° C. to about 240° C.

42. The process of clause 40 or 41, further comprising increasing the coupling temperature during the coupling step.

43. The process of any of clauses 40-42, further comprising increasing the coupling temperature from about 180° C. to about 240° C. during the coupling step.

44. The process of clause 42 or 43, wherein the coupling temperature is increased continuously for about 5 minutes to about 120 minutes, about 15 minutes to about 120 minutes, about 30 minutes to about 120 minutes, about 45 minutes to about 120 minutes, about 60 minutes to about 120 minutes, about 90 minutes to about 120 minutes, about 5 minutes to about 90 minutes, about 15 minutes to about 90 minutes, about 30 minutes to about 90 minutes, about 45 minutes to about 90 minutes, about 60 minutes to about 90 minutes, about 5 minutes to about 60 minutes, about 15 minutes to about 60 minutes, about 30 minutes to about 60 minutes, about 45 minutes to about 60 minutes, about 5 minutes to about 45 minutes, about 15 minutes to about 45 minutes, about 30 minutes to about 45 minutes, about 5 minutes to about 30 minutes, about 15 minutes to about 30 minutes, or about 5 minutes to about 15 minutes.

45. The process of any of clauses 42-44, wherein the coupling temperature is increased continuously for about 15 minutes to about 45 minutes.

46. The process of any of clauses 42-45, wherein the coupling temperature is increased continuously for about 30 minutes.

47. The process of any of clauses 42-46, wherein the aryl halide or aryl compound is added continuously at the same time that the coupling temperature is increased.

48. The process of any of the preceding clauses, wherein the aryl halide or aryl compound is the solvent of the coupling step.

49. The process of any of the preceding clauses, wherein the coupling step is performed at a pressure of about 15 psi to about 100 psi, about 30 psi to about 100 psi, about 40 psi to about 100 psi, about 15 psi to about 75 psi, about 30 psi to about 75 psi, about 40 psi to about 75 psi, about 15 psi to about 60 psi, about 30 psi to about 60 psi, about 40 psi to about 60 psi, about 15 psi to about 50 psi, about 30 psi to about 50 psi, about 40 psi to about 50 psi, or about 45 psi.

50. The process of any of the preceding clauses, wherein the coupling step is performed at a pressure of about 30 psi to about 60 psi.

51. The process of any of the preceding clauses, wherein the coupling step is performed at a pressure of about 45 psi.

52. The process of any of the preceding clauses, further comprising removing the aryl halide or aryl compound from the sulfone after the coupling step.

53. The process of any of the preceding clauses, further comprising removing the aryl halide or aryl compound from the sulfone by distillation after the coupling step.

54. The process of any of the preceding clauses, further comprising cooling the sulfone to a quenching temperature of about 50° C. to about 70° C.

55. The process of any of the preceding clauses, further comprising cooling the sulfone to a quenching temperature of about 60° C.

56. The process of any of the preceding clauses, further comprising extracting the sulfone after the coupling step.

57. The process of any of the preceding clauses, further comprising extracting the sulfone with an aromatic solvent after the coupling step.

58. The process of any of the preceding clauses, further comprising extracting the sulfone with toluene after the coupling step.

59. The process of any of clauses 56-58, wherein the extracting step is performed after removing the aryl halide or aryl compound from the sulfone.

60. The process of any of clauses 56-59, wherein the extracting step results in an amber colored solution comprising the sulfone.

61. The process of any of the preceding clauses, further comprising washing the sulfone with water.

62. The process of clause 61, wherein the washing step is performed after extracting the sulfone.

63. The process of any clause 61 or 62, wherein the washing step results in the sulfone being substantial free of the sulfonic acid.

64. The process of any of the preceding clauses, further comprising crystallizing the sulfone.

65. The process of clause 64, wherein the crystallizing step is performed after washing and extracting the sulfone.

66. The process of clause 64 or 65, wherein the crystallizing step results in the sulfone having a purity of greater than about 95%.

67. The process of any of clauses 64-66, wherein the crystallizing step results in the sulfone having a purity of greater than about 99%.

68. The process of any of clauses 64-67, wherein the crystallizing step results in the sulfone having a purity of about 99.9%.

69. The process of any of the preceding clauses, further comprising a first step comprising contacting a reactant of the formula

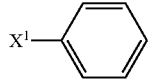

wherein $X^1$ is a H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, with sulfur trioxide to provide a first product mixture comprising the sulfonic acid.

70. The process of clause 69, wherein $X^1$ is Cl.

71. The process of clause 69 or 70, wherein the first step is performed under anhydrous conditions.

72. The process of any of clauses 69-71, wherein the concentration of water in the first product mixture is less than about 10 wt % water, less than about 5 wt % water, less than about 1 wt % water, or less than about 0.5 wt % water.

73. The process of any of clauses 69-72, wherein the concentration of water in the first product mixture is less than about 10 wt % water.

74. The process of any of clauses 69-73, wherein the first step is performed in a first reaction vessel and the first product mixture is transferred to a second reaction vessel after the first step for use in the coupling step.

75. The process of any of clauses 69-74, wherein the first step is performed at a sulfonation temperature of about 30° C. to about 100° C., about 40° C. to about 100° C., about 50° C. to about 100° C., about 60° C. to about 100° C., about 30° C. to about 90° C., about 40° C. to about 90° C., about 50° C. to about 90° C., about 60° C. to about 90° C., about 30° C. to about 80° C., about 40° C. to about 80° C., about 50° C. to about 80° C., about 60° C. to about 80° C., about 30° C. to about 75° C., about 40° C. to about 75° C., about 50° C. to about 75° C., or about 60° C. to about 75° C.

76. The process of any of clauses 69-75, wherein the first step occurs without external cooling.

77. The process of any of clauses 69-76, wherein the first product mixture comprises the sulfonic acid, the aryl halide, and the sulfone.

78. The process of any of clauses 69-77, wherein the first product mixture comprises about 53% of the sulfonic acid, about 6% of the aryl halide, and about 41% of the sulfone.

79. The process of any of clauses 69-78, wherein the coupling step comprises adding the catalyst to the first product mixture.

80. The process of any of clauses 69-79, wherein the coupling step comprises adding boric acid to the first product mixture.

81. The process of any of clauses 69-80, wherein the first step and the coupling steps are batch processes.

82. The process of any of clauses 69-80, wherein the first step is a batch process and the coupling step is a continuous process.

BRIEF DESCRIPTION OF THE DRAWING

FIG. 1 is a flow diagram showing one embodiment of a process for preparing dichlorodiphenyl sulfone from chlorobenzene sulfonic acid, include a coupling step and a purification step.

DETAILED DESCRIPTION

In accordance with Applicants' invention described herein, the embodiments of the numbered clauses provided in the summary above, or any combination thereof, are contemplated for combination with any of the embodiments described in the Detailed Description section of this patent application.

A process in accordance with a first embodiment includes a process for preparing a sulfone of the formula

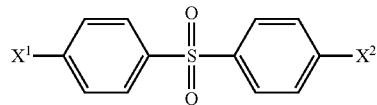

wherein $X^1$ and $X^2$ are each independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein. It will be understood that "aryl" may be combined with other groups, to form a functionalized aryl. By way of example, the combination of an "$C_6$-$C_{10}$ aryl" group, as described herein, with a "$C_1$-$C_6$ alkyl" group may be referred to as a —$C_1$-$C_6$ alkyl-($C_6$-$C_{10}$ aryl).

As used herein, "hydroxy" or "hydroxyl" refers to an —OH group.

As used herein, "alkoxy" refers to an —O-(alkyl) group, such as an —$OC_1$-$C_6$ alkyl. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl group, such as an —$OC_6$-$C_{10}$ aryl.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "cyano" refers to a —CN group.

The term "oxo" represents a carbonyl oxygen. For example, a cyclopentyl substituted with oxo is cyclopentanone.

As used herein, "halogen" refers to fluorine (F), chlorine (Cl), bromine (Br), and iodine (I). Halogens in their anionic forms or when covalently bonded to another atom may be alternatively referred to as "halides." Illustratively, a bond between carbon and a halogen is understood to be a covalent bond and may be alternatively referred to as a carbon-halogen or carbon-halide bond.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl is independently optionally substituted by halogen" means that a halogen may be but need not be present on the $C_1$-$C_6$ alkyl replacement of a hydrogen atom for each halogen group, and the description includes situations where a $C_1$-$C_6$ alkyl, for example, is substituted with a halogen, and situations where a $C_1$-$C_6$ alkyl, for example, is not substituted with a halogen.

In some embodiments, the process of the present disclosure additionally includes a first step comprising contacting a reactant of the formula

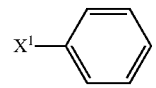

wherein $X^1$ is H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, with sulfur trioxide. The first step provides a first product mixture that includes a sulfonic acid. In some embodiments, $X^1$ is halogen. In some embodiments, $X^1$ is Cl.

The first step is generally described by the equation:

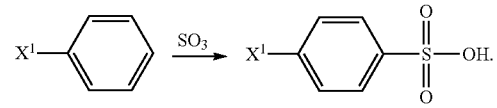

Illustratively, the first step may be performed in a first reaction vessel and the product mixture produced by the first step may be transferred to a second reaction vessel after the first step for use in a coupling step.

The product mixture of the first step may comprise a sulfonic acid, an aryl halide, and a sulfone. The sulfonic acid may be chlorobenzene sulfonic acid, the aryl halide may be monocholorbenzene, and the sulfone may be dichlorodiphenyl sulfone. In some embodiments, the first product mixture comprises about 53% of the sulfonic acid, about 6% of the aryl halide, and about 41% of the sulfone.

The process of the present disclosure comprises a coupling step comprising contacting a sulfonic acid of the formula

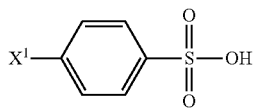

wherein $X^1$ is a halogen, with an aryl halide of the formula

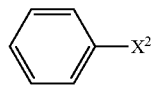

wherein $X^2$ is H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl. In some embodiments, $X^2$ is halogen. In some embodiments, $X^2$ is Cl.

The coupling step is generally described by the equation:

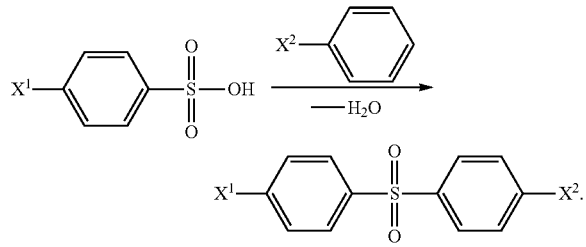

It is understood that when chemical equations are shown herein, additional reactants, additional reaction components, byproducts, additional products, and impurities that are not shown in the chemical equations may be present.

It is also understood that during the contacting step of the coupling step, a bond is formed between a carbon of the aryl halide and the sulfur of sulfur trioxide. Without being bound by theory, the bond may form as a result of an electrophilic aromatic substitution reaction in which sulfur trioxide replaces an aryl hydrogen.

The coupling step occurs in the presence of a catalyst, and resulting water is removed during the coupling step. As used herein, "resulting water" describes water formed as a result of the coupling step. The combination of a catalyst and the absence of water results in a process that produces sulfone products in enhanced yields with enhanced selectivity compared to processes known in the art.

In one aspect of the present disclosure, the coupling step may comprise adding the catalyst to the product mixture of the first step. In some embodiments, the catalyst is boric acid.

In another aspect of the present disclosure, the first step and the coupling steps are separate steps of a batch process. In another aspect of the present disclosure, the first step and the coupling steps are separate steps of a continuous process. In other embodiments, the first step is a batch process, and the coupling step is a continuous process.

In some embodiments of the process described herein, $X^1$ and $X^2$ are Cl. In such embodiments, the sulfone is of the formula

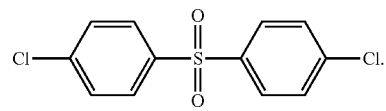

When $X^1$ and $X^2$ are Cl, the first step is generally described by the equation:

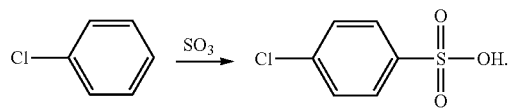

and the coupling step is generally described by the equation:

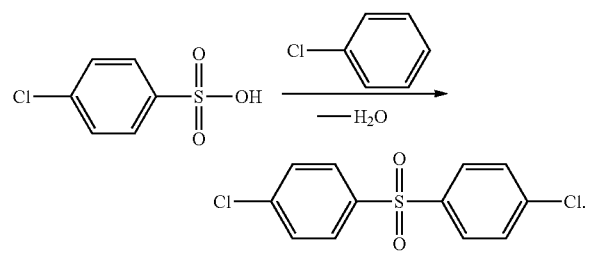

As used herein, yield describes the actual amount of a product produced by a reaction relative to the theoretical maximum amount of the product predicted by a stoichiometric calculation. For example, determining yield by the sulfone relative to the sulfonic acid may include determining the theoretical maximum amount of the sulfone based on the number of moles of the sulfonic acid in the initial reaction mixture. Calculating yield is well understood in the art.

As used herein, crude yield describes yield determined after reaction workup or quenching, prior to additional purification steps. As used herein, purified yield describes yield determined after reaction workup or quenching and after one or more purification steps.

As previously stated, the process produces sulfone products with enhanced yields. In some embodiments, the crude yield of the coupling step, as determined by the sulfone relative to the sulfonic acid, is about 50% to about 100%, about 55% to about 100%, about 60% to about 100%, about 65% to about 100%, about 70% to about 100%, about 75% to about 100%, about 80% to about 100%, about 85% to about 100%, about 50% to about 95%, about 55% to about 95%, about 60% to about 95%, about 65% to about 95%, about 70% to about 95%, about 75% to about 95%, about 80% to about 95%, about 85% to about 95%, about 50% to about 90%, about 55% to about 90%, about 60% to about 90%, about 65% to about 90%, about 70% to about 90%, about 75% to about 90%, about 80% to about 90%, or about 85% to about 90%. For example, the crude yield of the coupling step, as determined by the sulfone relative to the sulfonic acid, may be about 60% to about 95%. Additionally, the crude yield of the coupling step, as determined by the sulfone relative to the sulfonic acid, may be about 82% to about 93%.

In some embodiments, the purified yield of the coupling step, as determined by the sulfone relative to the sulfonic acid, is about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, 40% to about 90%, about 45% to about 90%, about 50% to about 90%, about 55% to about 90%, about 60% to about 90%, about 65% to about 90%, about 70% to about 90%, about 75% to about 90%, about 80% to about 90%, 40% to about 85%, about 45% to about 85%, about 50% to about 85%, about 55% to about 85%, about 60% to about 85%, about 65% to about 85%, about 70% to about 85%, about 75% to about 85%, or about 80% to about 85%. For example, the purified yield of the coupling step, as determined by the sulfone relative to the sulfonic acid, may be about 50% to about 85%. Additionally, the purified yield of the coupling step, as determined by the sulfone relative to the sulfonic acid, may be about 70% to about 75%.

It is understood that values preceded by the word "about" include both an exact value and about that value. For example, "about 90%" describes both exactly 90% and about 90%.

In some embodiments, the coupling step is initiated under anhydrous conditions. For example, in some embodiments, the coupling step is initiated with less than about 10 wt % water, less than about 5 wt % water, less than about 1 wt % water, or less than about 0.5 wt % water. In some embodiments, the coupling step is initiated with less than about 10 wt % water.

In some embodiments, the resulting water in the coupling step is removed continuously during the coupling step. For example, the resulting water may be removed by distillation.

In certain embodiments, the concentration of water throughout the coupling step is less than about 10 wt % water, less than about 5 wt % water, less than about 1 wt % water, or less than about 0.5 wt % water. For example, the concentration of water throughout the coupling step may be less than about 10 wt % water.

In some embodiments, the coupling step is performed without a dehydrating reagent. As used herein, a "dehydrating reagent" is a reagent that prevents the production of water as a reaction product during the coupling step by reacting with other reactants involved in sulfone formation. An example of a dehydrating reagent is trifluoroacetic anhydride when used with cholorbenzene and sulfuric acid.

In additional embodiments, the concentration of the catalyst relative to all components of the coupling step, when the coupling step is initiated, is about 0.1 wt % to about 10 wt %, about 0.1 wt % to about 5 wt %, about 0.5 wt % to about 2 wt %, about 0.7 wt % to about 1.1 wt %, or about 0.9 wt %. Illustratively, the concentration of the catalyst relative to all components of the coupling step, when the coupling step is initiated, may be about 0.1 wt % to about 5 wt %. Additionally, the concentration of the catalyst relative to all components of the coupling step, when the coupling step is initiated, may be about 0.7 wt % to about 1.1 wt %.

Moreover, amount of the catalyst relative to the sulfonic acid, when the coupling step is initiated, may be about 0.01 equivalent to about 1 equivalent, about 0.01 equivalent to about 0.5 equivalent, about 0.01 equivalent to about 0.1 equivalent, about 0.01 to about 0.075 equivalent, about 0.02 equivalent to about 1 equivalent, about 0.02 equivalent to about 0.5 equivalent, about 0.02 equivalent to about 0.1 equivalent, about 0.02 to about 0.075 equivalent, about 0.025 equivalent, or about 0.05 equivalent. Illustratively, the concentration of the catalyst relative to the sulfonic acid, when the coupling step is initiated, may be about 0.01 equivalent to about 0.1 equivalent. Additionally, the concentration of the catalyst relative to the sulfonic acid, when the coupling step is initiated, may be about 0.025 equivalent to about 0.05 equivalent.

In some embodiments, the catalyst is a boron catalyst, an iron catalyst, a zinc catalyst, a tin catalyst, a titanium catalyst, a zirconium catalyst, a bismuth catalyst, an antimony catalyst, a silica catalyst, a metal sulfate catalyst, a metal oxide catalyst, a sulfonic acid catalyst, an iodine catalyst, or a combination thereof. For example, the catalyst may be aluminum oxide, antimony oxide, zirconium oxide, bismuth oxide, boric anhydride, boric acid, ferric oxide, stannic oxide, titanium oxide, titanium sulfate, zinc oxide, iodine, lithium iodide, methane sulfonic acid, trifluoromethane sulfonic acid, silica, or dimethylsulfate. In certain embodiments, the catalyst may be aluminum oxide. In certain embodiments, the catalyst may be antimony oxide. In certain embodiments, the catalyst may be zirconium oxide. In certain embodiments, the catalyst may be bismuth oxide. In certain embodiments, the catalyst may be boric anhydride. In certain embodiments, the catalyst may be boric acid. In certain embodiments, the catalyst may be ferric oxide. In certain embodiments, the catalyst may be stannic oxide. In certain embodiments, the catalyst may be titanium oxide. In certain embodiments, the catalyst may be titanium sulfate. In certain embodiments, the catalyst may be zinc oxide. In certain embodiments, the catalyst may be iodine. In certain embodiments, the catalyst may be lithium iodide. In certain embodiments, the catalyst may be methane sulfonic acid. In certain embodiments, the catalyst may be trifluoromethane sulfonic acid. In certain embodiments, the catalyst may be silica. In certain embodiments, the catalyst may be dimethylsulfate.

In some embodiments, the coupling step results in less than 20% of a 2,4' isomer of the formula

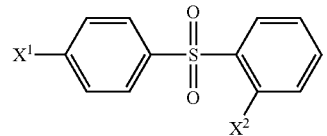

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 2,4' isomer relative to all sulfone products. In other embodiments, the coupling step results in less than 10% of the 2,4' isomer. Illustratively, $X^1$ and $X^2$ may be Cl.

In additional embodiments, the coupling step results in less than 20% of a 3,4' isomer of the formula

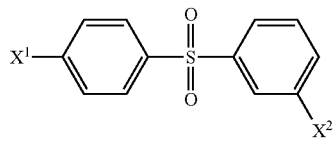

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$OC_1$-$C_6$ alkyl or —$OC_6$-$C_{10}$ aryl, as determined by the 3,4' isomer relative to all sulfone products. In other embodiments, the coupling step results in less than 10% of the 3,4' isomer. Illustratively, $X^1$ and $X^2$ may be Cl.

In some embodiments, the coupling step results in less than 20% of a 2,4' isomer of the formula

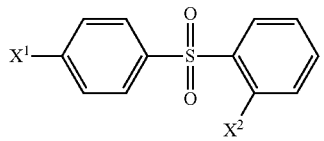

wherein $X^1$ and $X^2$ are independently halogen, as determined by the 2,4' isomer relative to all sulfone products. In other embodiments, the coupling step results in less than 10% of the 2,4' isomer. Illustratively, $X^1$ and $X^2$ may be Cl.

In additional embodiments, the coupling step results in less than 20% of a 3,4' isomer of the formula

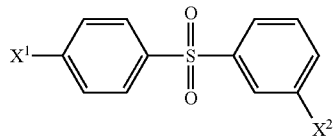

wherein $X^1$ and $X^2$ are independently halogen, as determined by the 3,4' isomer relative to all sulfone products. In other embodiments, the coupling step results in less than 10% of the 3,4' isomer. Illustratively, $X^1$ and $X^2$ may be Cl.

In some embodiments, the aryl halide or aryl compound is added to the sulfonic acid continuously during the coupling step. For example, the aryl halide may be added to the sulfonic acid continuously for about 0.5 hour to about 20 hours, about 1 hour to about 20 hours, about 2 hours to about 20 hours, about 7 hours to about 20 hours, about 9 hours to about 20 hours, about 10 hours to about 20 hours, about 0.5 hour to about 15 hours, about 1 hour to about 15 hours, about 2 hours to about 15 hours, about 7 hours to about 15 hours, about 9 hours to about 15 hours, about 10 hours to about 15 hours, about 0.5 hour to about 13 hours, about 1 hour to about 13 hours, about 2 hours to about 13 hours, about 7 hours to about 13 hours, about 9 hours to about 13 hours, about 0.5 hour to about 12 hours, about 1 hour to about 12 hours, about 2 hours to about 12 hours, about 7 hours to about 12 hours, about 9 hours to about 12 hours, about 10 hours to about 12 hours, or about 10 hours. The aryl halide may be added to the sulfonic acid continuously for about 7 hours to about 13 hours. Additionally, the aryl halide may be added to the sulfonic acid continuously for about 9 hours to about 12 hours. Moreover, the aryl halide may be added to the sulfonic acid continuously for about 10 hours.

In some embodiments, the aryl halide or aryl compound is added to the sulfonic acid continuously at the same time that water is removed continuously from the sulfonic acid. In certain embodiments, the aryl halide or aryl compound is added to the sulfonic acid continuously at the same time that wet chlorobenzene is removed continuously from the sulfonic acid.

Illustratively, the aryl halide or aryl compound may be added at a flow rate of about 0.1 mL/min to about 10 mL/min, about 0.5 mL/min to about 5 mL/min, about 0.5 mL/min to about 3 mL/min, or about 1.5 mL/min. More specifically, the aryl halide may be added at a flow rate of about 1.5 mL/min.

In some embodiments, the coupling step is performed at a coupling temperature of about 150° C. to about 280° C., about 160° C. to about 280° C., about 170° C. to about 280° C., about 180° C. to about 280° C., about 150° C. to about 260° C., about 160° C. to about 260° C., about 170° C. to about 260° C., about 180° C. to about 260° C., about 150° C. to about 240° C., about 160° C. to about 240° C., about 170° C. to about 240° C., or about 180° C. to about 240° C. In certain embodiments, the coupling step is performed at a coupling temperature of about 180° C. to about 240° C.

In one aspect of the present disclosure, the coupling temperature may be increased during the coupling step. The process may include increasing the coupling temperature from about 180° C. to about 240° C. during the coupling step. The coupling temperature may be increased continuously for about 5 minutes to about 120 minutes, about 15 minutes to about 120 minutes, about 30 minutes to about 120 minutes, about 45 minutes to about 120 minutes, about 60 minutes to about 120 minutes, about 90 minutes to about 120 minutes, about 5 minutes to about 90 minutes, about 15 minutes to about 90 minutes, about 30 minutes to about 90 minutes, about 45 minutes to about 90 minutes, about 60 minutes to about 90 minutes, about 5 minutes to about 60 minutes, about 15 minutes to about 60 minutes, about 30 minutes to about 60 minutes, about 45 minutes to about 60 minutes, about 5 minutes to about 45 minutes, about 15 minutes to about 45 minutes, about 30 minutes to about 45 minutes, about 5 minutes to about 30 minutes, about 15 minutes to about 30 minutes, or about 5 minutes to about 15 minutes. In certain embodiments, the coupling temperature is increased continuously for about 15 minutes to about 45 minutes. In some embodiments, the coupling temperature is increased continuously for about 30 minutes.

Another aspect of the present disclosure is that the aryl halide or aryl compound may be added continuously at the same time that the coupling temperature is increased.

Illustratively, the aryl halide or aryl compound may be the solvent of the coupling step.

In some embodiments, the coupling step is performed at a pressure of about 15 pounds per square inch (psi) to about 100 psi, about 30 psi to about 100 psi, about 40 psi to about 100 psi, about 15 psi to about 75 psi, about 30 psi to about 75 psi, about 40 psi to about 75 psi, about 15 psi to about 60 psi, about 30 psi to about 60 psi, about 40 psi to about 60 psi, about 15 psi to about 50 psi, about 30 psi to about 50 psi, about 40 psi to about 50 psi, or about 45 psi. For example, the coupling step may be performed at a pressure of about 30 psi to about 60 psi. Additionally, coupling step may be performed at a pressure of about 45 psi.

In illustrative embodiments, the process includes one or more purification methods. In some embodiments, the aryl halide or aryl compound is removed from the sulfone after the coupling step. The aryl halide or aryl compound may be removed from the sulfone by distillation.

In certain embodiments, the sulfone is cooled to a quenching temperature of about 50° C. to about 70° C. For example, the process may include cooling the sulfone to a quenching temperature of about 60° C.

In some embodiments, the process includes extracting the sulfone after the coupling step. The sulfone may be extracted with an aromatic solvent after the coupling step. In some embodiments, the sulfone is extracted with toluene after the coupling step. The extracting step may be performed after removing the aryl halide or aryl compound from the sulfone. In certain embodiments, the extracting step results in an amber colored solution comprising the sulfone.

The process of the present disclosure may further comprise washing the sulfone with water. The washing step may be performed after extracting the sulfone. Illustratively, the washing step may result in the sulfone being substantial free of the sulfonic acid.

In certain embodiments, the process may include crystallizing the sulfone. A crystallizing step may be performed after washing and extracting the sulfone. The crystallizing step may result in the sulfone having a purity of greater than about 95%. In some embodiments, the crystallizing step results in the sulfone having a purity of greater than about 99%. For example, the crystallizing step may result in the sulfone having a purity of about 99.9%.

In some embodiments, the first step of the process of the present disclosure is performed under anhydrous conditions. Specifically, the concentration of water in the first product mixture may be less than about 10 wt % water, less than about 5 wt % water, less than about 1 wt % water, or less than about 0.5 wt % water. In certain embodiments, the concentration of water in the first product mixture is less than about 10 wt % water.

Another aspect of the present disclosure is that the first step may performed at a sulfonation temperature of about 30° C. to about 100° C., about 40° C. to about 100° C., about 50° C. to about 100° C., about 60° C. to about 100° C., about 30° C. to about 90° C., about 40° C. to about 90° C., about 50° C. to about 90° C., about 60° C. to about 90° C., about 30° C. to about 80° C., about 40° C. to about 80° C., about 50° C. to about 80° C., about 60° C. to about 80° C., about 30° C. to about 75° C., about 40° C. to about 75° C., about 50° C. to about 75° C., or about 60° C. to about 75° C. In some embodiments, the first step occurs without external cooling.

Now referring to FIG. 1, a process for preparing dichlorodiphenyl sulfone from chlorobenzene sulfonic acid is shown. The process includes a coupling step and a purification step.

The coupling step includes first combining chlorobenzene sulfonic acid, monochlorobenzene (also referred to herein as chlorobenzene), and boric acid in a DCDPS reactor (Step 1). After chlorobenzene sulfonic acid, monochlorobenzene, and boric acid are combined in the DCDPS reactor, monochlorobenzene is added (Step 2) while wet monochlorobenezene is removed (Step 3). The coupling step results in a crude dichlorodiphenyl sulfone mixture.

The purification step includes transferring the crude dichlorodiphenyl sulfone mixture to another vessel fitted with a Dean-Stark trap (Step 4). Water is added to the crude dichlorodiphenyl sulfone mixture (Step 5) while wet monochlorbenzene is removed (Step 6). Dichlorophenyl sulfone is obtained by filtration (Step 7). Chlorobenzene sulfonic acid is recovered by evaporation (Step 8).

Advantageously, the process of the present disclosure efficiently affords 4,4'-dichlorodiphenylsulfone in high yield and high selectivity with minimal byproduct formation, as further demonstrated by the Examples below.

EXAMPLES

TABLE 1

Yields and Ratios of Sulfone Isomers for Examples CE-1 and 1-7

| | | Isomers | | |
| --- | --- | --- | --- | --- |
| Example | Yield | 4,4' Isomer | 2,4' Isomer | 3,4' Isomer |
| U.S. Pat. No. 4,983,773, Example 2 reported results. | 84% | 84.8% | 7.8% | 7.4% |
| CE-1 | 14% | 60.5% | 2.7% | 36.8% |
| 1 | 85% (73%*) | 87.3% | 8.0% | 4.7% |
| 2 | 89% | 86.7% | 8.2% | 5.1% |
| 3 | 82% | 88.6% | 8.0% | 3.4% |
| 4 | 85% | 86.0% | 10.0% | 4.0% |
| 5 | 89% | 86.4% | 8.4% | 5.2% |
| 6 | 87% | 86.7% | 8.2% | 5.1% |
| 7 | 81% | 82.1% | 10.1% | 7.8% |

*Recrystllized yield

Comparative Example 1 (CE-1): Preparation of 4,4'-Dichlorodiphenyl Sulfone Using Boric Acid Following Procedure of U.S. Pat. No. 4,983,773 (Jan. 8, 1991), Example 2

Repetition of the U.S. Pat. No. 4,983,773 process, as described below, resulted in a mixture that could not be purified by the same methods reported therein. Additionally, repetition of the U.S. Pat. No. 4,983,773 process resulted in significantly lower yield and significantly lower selectivity than reported therein.

A 0.5 L autoclave fitted with an addition pump for chlorobenzene, backflow regulator, and condenser was charged with 50 g conc. sulfuric acid, 100 g chlorobenzene, and 1.5 g boric acid catalyst. The back flow regulator was set to 65 psi and the contents of the autoclave were heated to 180° C. at which point condensate began to drip from the condenser. Chlorobenzene addition was started at a flow rate of 1.5 mL/min and heating was continued until the reactor reached 240° C. (approximately 1 hour). The chlorobenzene addition was continued for a total of 16 hours while distilling off excess chlorobenzene and any water formed during the reaction. The reactor was cooled to 120° C. the autoclave was opened and found to contain a 69 g of a black tar in unreacted chlorobenzene. Analysis showed it to contain 60.5% 4,4'-dichlorodiphenyl sulfone relative to the other dichlorodiphenyl sulfone isomers (see Table 1), but many other unidentified byproducts were also present. The amount of 4.4'-dichlorodiphenyl sulfone in the tar corresponded to a 14% yield relative to reacted chlorobenzene. Attempts to separate the desired material from the byproducts were unsuccessful. This included pouring the tarry reaction crude into water and extracting the aqueous layer with toluene, chlorobenzene, or 2-methyltetrahydrofuran. All extraction attempts resulted in black emulsions whereby the organic and water components could not be separated. Attempts also included steam distillation of the reaction crude to remove volatile materials, but this provided a black emulsion that could not be filtered.

Example 1: Improved Process for Preparing 4,4'-Dichlorodiphenyl Sulfone Using Boric Acid Catalyst A 500 mL round-bottom flask containing 145 g chlorobenzene was treated with gaseous 42 g sulfur trioxide over a 3 hour period so as to keep the internal temperature of the reaction vessel at or below 75° C. without external cooling. Analysis of the resultant solution showed it to contain 53.4% 4-chlorobenzenesulfonic acid, 5.8% 4,4'-dichlorodiphenyl sulfone, and 40.8% chlorobenzene. This solution (173 g) and 1.5 g boric acid were charged to the autoclave of Example 1. The back flow regulator was set to 45 psi and the contents of the autoclave were heated to 180° C. at which point condensate began to drip from the condenser. Chlorobenzene addition was started at a flow rate of 1.5 mL/min and heating was continued until the reactor temperature reached 240° C. (approximately 30 minutes). The chlorobenzene addition was continued for a total of 10 hours while simultaneously removing wet chlorobenzene though the condenser. At the end of the addition the autoclave contained 50 g chlorobenzene, 29.3 g 4-chlorobenzenesulfonic acid, and 102 g of 4,4'-dichlorodiphenylsulfone and related isomers (85% yield when adjusted for unreacted chlorobenzenesulfonic acid and subtraction of unwanted isomers). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 29.3 g unreacted 4-chlorobenzenesulfonic acid. Analysis of the toluene extracts determined 87.3% 4,4'-dichlorodiphenylsulfone compared to the other dichlorodiphenyl sulfone isomers (see Table 1). The amber colored organic layers were concentrated, and crystallization provided 69 g of 99.9% pure 4,4'-dichlorodiphenyl sulfone as colorless needles (73% yield adjusted for unreacted chlorobenzenesulfonic acid).

Example 2: Improved Process for Preparing 4,4'-Dichlorodiphenyl Sulfone Using Boric Acid Catalyst and Purchased 4-Chlorobenzenesulfonic Acid The autoclave of example 1 was charged with 104.1 g 4-chlorobenzenesulfonic acid (tech grade, 87.4% by weight, 0.47 Mol) and 1.5 g boric acid. The back flow regulator was set to 45 psi and the contents of the autoclave were heated to 180° C. at which point condensate began to drip from the condenser. Chlorobenzene addition was started at a flow rate of 1.5 mL/min and heating was continued until the reactor temperature reached 240° C. (approximately 30 minutes). The chlorobenzene addition was continued for a total of 10 hours while simultaneously removing wet chlorobenzene though the condenser. The contents of the autoclave were transferred to a round-bottom flask fitted with a Dean-Stark trap and containing 280 g water. The remaining 65 g of chlorobenzene was removed by steam distillation and the resultant grey slurry was cooled and filtered. The filtrate was dewatered to afford 28.3 g unreacted 4-chlorobenzenesulfonic acid. The filtered grey solid was dried to provide 95.4 g of 4,4'-dichlorodiphenylsulfone in 86.7% isomeric purity (89% yield adjusted for unreacted chlorobenzenesulfonic acid).

Example 3: Preparation of 4,4'-Dichlorodiphenyl Sulfone Using Ferric Oxide Catalyst The procedure of Example 2 was followed except 0.40 g of ferric oxide was used in place of boric acid, the chlorobenzene addition rate was 1.0 mL/min, and the reaction time was 7.4 hours. 28.3 g of unreacted 4-chlorobenzenesulfonic acid was isolated and 82.3 g of 4,4'-dichlorodiphenyl sulfone was obtained in 88.6% isomeric purity (88% yield adjusted for unreacted chlorobenzenesulfonic acid).

Example 4: Preparation of 4,4'-Dichlorodiphenyl Sulfone Using Stannic Oxide Catalyst The procedure of Example 3 was followed except 3.66 g of stannic oxide was used in place of boric acid, the chlorobenzene addition rate was 1.0 mL/min, and the reaction time was 7.4 hours. 24.4 g unreacted 4-chlorobenzenesulfonic acid was isolated and 84.5 g of 4,4'-dichlorodiphenyl sulfone was obtained in 88.6% isomeric purity (85% yield adjusted for unreacted chlorobenzenesulfonic acid).

Example 5: Preparation of 4,4'-Dichlorodiphenyl Sulfone Using Titanium Sulfate Catalyst The procedure of Example 3 was followed except 7.3 g of titanium sulfate was used in place of boric acid, the chlorobenzene addition rate was 1.0 mL/min, and the reaction time was 7.4 hours. 27.4 g unreacted 4-chlorobenzenesulfonic acid was isolated and 87.5 g of 4,4'-dichlorodiphenyl sulfone was obtained in 86.4% isomeric purity (89% yield adjusted for unreacted chlorobenzenesulfonic acid).

Example 6: Preparation of 4,4'-Dichlorodiphenyl Sulfone Using Iodine Catalyst The procedure of Example 3 was followed except 3.16 g of iodine was used in place of boric acid, the chlorobenzene addition rate was 1.0 mL/min, and the reaction time was 12 hours. 27.6 g unreacted 4-chlorobenzenesulfonic acid was isolated and 91.8 g of 4,4'-dichlorodiphenyl sulfone was obtained in 86.7% isomeric purity (87% yield adjusted for unreacted chlorobenzenesulfonic acid).

Example 7: Preparation of 4,4'-Dichlorodiphenyl Sulfone

The procedure of Example 3 was followed except 4.0 g of lithium iodide was used in place of boric acid, the chlorobenzene addition rate was 1.0 mL/min, and the reaction time was 7.4 hours. 44.1 g unreacted 4-chlorobenzenesulfonic acid was isolated and 59.7 g of 4,4'-dichlorodiphenyl sulfone was obtained in 82.1% isomeric purity (81% yield adjusted for unreacted chlorobenzenesulfonic acid).

Example 8: Improved Process for Preparing 4,4'-Dichlorodiphenyl Sulfone Using Boric Acid Catalyst (B400-07)

A solution of 100 g monochlorobenzene, 95.20 g chlorobenzene sulfonic acid, and 1.5 g boric acid (0.05 equiv) were charged to the autoclave of Example 1. The solution contained 7.27 g water. The back flow regulator was set to 45 psi and the contents of the autoclave were heated to 180° C. at which point condensate began to drip from the condenser. Chlorobenzene addition was started at a flow rate of 1 mL/min until 454.40 g chlorobenzene was added and heating was continued until the reactor temperature reached 240° C. The chlorobenzene addition was continued while simultaneously removing wet chlorobenzene though the condenser. At the end of the addition the autoclave contained 56.00 g chlorobenzene, 35.68 g 4-chlorobenzenesulfonic acid, and 82.30 g of 4,4'-dichlorodiphenylsulfone and related isomers (58.0% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 35.68 g unreacted 4-chlorobenzenesulfonic acid. Analysis of the toluene extracts determined 85.8% 4,4'-dichlorodiphenylsulfone, 8.5% 2,4'-dichlorodiphenylsulfone, and 5.7% 3,4'-dichlorodiphenylsulfone, each compared to the other dichlorodiphenyl sulfone isomers.

Example 9: Improved Process for Preparing 4,4'-Dichlorodiphenyl Sulfone Using Ferric Oxide Catalyst (B400-08)

A solution of 100 g monochlorobenzene, 95.75 g chlorobenzene sulfonic acid, and 0.40 g $Fe_2O_3$ (0.025 equiv) were charged to the autoclave of Example 1. The solution contained 7.32 g water. The back flow regulator was set to 45 psi and the contents of the autoclave were heated to 180° C. at which point condensate began to drip from the condenser. Chlorobenzene addition was started at a flow rate of 1 mL/min until 452.20 g chlorobenzene was added and heating was continued until the reactor temperature reached 240° C. The chlorobenzene addition was continued while simultaneously removing wet chlorobenzene though the condenser. At the end of the addition the autoclave contained 39.00 g chlorobenzene, 36.17 g 4-chlorobenzenesulfonic acid, and 82.29 g of 4,4'-dichlorodiphenylsulfone and related isomers (57.6% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 36.17 g unreacted 4-chlorobenzenesulfonic acid. Analysis of the toluene extracts determined 88.6% 4,4'-dichlorodiphenylsulfone, 8.0% 2,4'-dichlorodiphenylsulfone, and 3.4% 3,4'-dichlorodiphenylsulfone, each compared to the other dichlorodiphenyl sulfone isomers.

Example 10: Improved Process for Preparing 4,4'-Dichlorodiphenyl Sulfone Using Stannic Oxide Catalyst (B400-24)

A solution of 100 g monochlorobenzene, 95.80 g chlorobenzene sulfonic acid, and 3.66 g $SnO_2$ (0.05 equiv) were charged to the autoclave of Example 1. The solution contained 7.32 g water. The back flow regulator was set to 45 psi and the contents of the autoclave were heated to 180° C. at which point condensate began to drip from the condenser. Chlorobenzene addition was started at a flow rate of 1 mL/min until 482.20 g chlorobenzene was added and heating was continued until the reactor temperature reached 240° C. The chlorobenzene addition was continued while simultaneously removing wet chlorobenzene though the condenser. At the end of the addition the autoclave contained 47.00 g chlorobenzene, 34.45 g 4-chlorobenzenesulfonic acid, and 84.50 g of 4,4'-dichlorodiphenylsulfone and related isomers (59.2% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 34.45 g unreacted 4-chlorobenzenesulfonic acid. Analysis of the toluene extracts determined 86.0% 4,4'-dichlorodiphenylsulfone, 10.0% 2,4'-dichlorodiphenylsulfone, and 4.0% 3,4'-dichlorodiphenylsulfone, each compared to the other dichlorodiphenyl sulfone isomers.

Example 11: Improved Process for Preparing 4,4'-Dichlorodiphenyl Sulfone Using Titanium Sulfate Catalyst (B400-29)

A solution of 100 g monochlorobenzene, 95.80 g chlorobenzene sulfonic acid, and 1.5 g $TiSO_4$ were charged to the autoclave of Example 1. The solution contained 7.32 g water. The back flow regulator was set to 45 psi and the contents of the autoclave were heated to 180° C. at which point condensate began to drip from the condenser. Chlorobenzene addition was started at a flow rate of 1 mL/min until 473.70 g chlorobenzene was added and heating was continued until the reactor temperature reached 240° C. The chlorobenzene addition was continued while simultaneously removing wet chlorobenzene though the condenser. At the end of the addition the autoclave contained 49.00 g chlorobenzene, 37.36 g 4-chlorobenzenesulfonic acid, and 87.50 g of 4,4'-dichlorodiphenylsulfone and related isomers (61.3% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 37.36 g unreacted 4-chlorobenzenesulfonic acid. Analysis of the toluene extracts determined 86.4% 4,4'-dichlorodiphenylsulfone, 8.4% 2,4'-dichlorodiphenylsulfone, and 5.2% 3,4'-dichlorodiphenylsulfone, each compared to the other dichlorodiphenyl sulfone isomers.

Example 12: Improved Process for Preparing 4,4'-Dichlorodiphenyl Sulfone Using Iodine Catalyst (B400-36)

A solution of 74.77 g monochlorobenzene, 89.41 g chlorobenzene sulfonic acid, and 1.5 g $I_2$ were charged to the autoclave of Example 1. The solution contained 0.1 g water and 7.74 g dichlorodiphenylsulfone. The back flow regulator was set to 45 psi and the contents of the autoclave were heated to 180° C. at which point condensate began to drip from the condenser. Chlorobenzene addition was started at a flow rate of 1 mL/min until 760.84 g chlorobenzene was added and heating was continued until the reactor temperature reached 240° C. The chlorobenzene addition was continued while simultaneously removing wet chlorobenzene though the condenser. At the end of the addition the autoclave contained 48.00 g chlorobenzene, 28.90 g 4-chlorobenzenesulfonic acid, and 91.80 g of 4,4'-dichlorodiphenylsulfone and related isomers (68.9% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 28.90 g unreacted 4-chlorobenzenesulfonic acid. Analysis of the toluene extracts determined 86.7% 4,4'-dichlorodiphenylsulfone, 8.2% 2,4'-dichlorodiphenylsulfone, and 5.1% 3,4'-dichlorodiphenylsulfone, each compared to the other dichlorodiphenyl sulfone isomers.

Example 13: Improved Process for Preparing 4,4'-Dichlorodiphenyl Sulfone Using Lithium Iodide Catalyst (B400-40)

A solution of 105.00 g monochlorobenzene, 96.70 g chlorobenzene sulfonic acid, and 1.5 g LiI were charged to the autoclave of Example 1. The solution contained 7.39 g water. The back flow regulator was set to 45 psi and the contents of the autoclave were heated to 180° C. at which point condensate began to drip from the condenser. Chlorobenzene addition was started at a flow rate of 1 mL/min until 487.70 g chlorobenzene was added and heating was continued until the reactor temperature reached 240° C. The chlorobenzene addition was continued while simultaneously removing wet chlorobenzene though the condenser. At the end of the addition the autoclave contained 35.00 g chlorobenzene, 44.10 g 4-chlorobenzenesulfonic acid, and 59.73 g of 4,4'-dichlorodiphenylsulfone and related isomers (41.4% yield when adjusted for unreacted chlorobenzenesulfonic acid). The contents of the autoclave were transferred to a round-bottom flask fitted with a Dean-Stark trap. The remaining chlorobenzene was then steam distilled from the mixture while returning the water back into the flask. The resultant grey slurry was cooled to 60° C. and extracted twice with toluene. The combined organic layers were washed once with water, and the combined aqueous extracts dewatered to afford 44.10 g unreacted 4-chlorobenzenesulfonic acid. Analysis of the toluene extracts determined 82.1% 4,4'-dichlorodiphenylsulfone, 10.1% 2,4'-dichlorodiphenylsulfone, and 7.8% 3,4'-dichlorodiphenylsulfone, each compared to the other dichlorodiphenyl sulfone isomers.

Example 14: Survey of Catalysts

A series of catalysts were surveyed for the production of DCDPS using the following general procedure.

A reaction vessel was charged with 113 g of chlorobenzene and catalyst (See table 2 for catalysts and amounts used). A gentle flow of $SO_3$ was introduced into the reaction vessel until a total of 41.5 g of $SO_3$ was delivered to the reaction vessel. During this time, the internal temperature of the reaction vessel reached a maximum of 75° C. The mixture was heated to 200° C. during and most of the solvent distilled off. This hot residue was treated with 275 g chlorobenzene over a 4 hour period via syringe pump while driving off excess chlorobenzene and any water formed. At the end of the 4 hour period, the reaction was quenched with water (125 mL) and the resultant solid filtered and air dried for 3-4 hours to provide crude DCDPS as a grey solid.

TABLE 2

Yields of Sulfone from Example 14

| Catalyst (equiv.) | DCDPS Yield |
| --- | --- |
| $CH_3SO_4CH_3$ (0.05 equiv) | 26% |
| $PO(OCH_3)_3$ (0.05 equiv) | 12% |
| $CH_3SO_3H$ (0.01 equiv) | 29% |
| $CF_3SO_3H$ (0.01 equiv) | 32% |
| ZnO (0.01 equiv) | 31% |
| $ZrO_2$ (0.01 equiv) | 34% |
| $Bi_2O_3$ (0.01 equiv) | 31% |
| $Sb_2O_3$ (0.01 equiv) | 29% |
| $B_2O_3$ (0.01 equiv) | 34% |

What is claimed is:

1. A process for preparing a sulfone of the formula

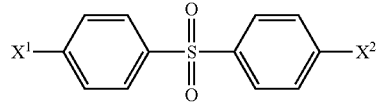

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl; the process comprising
a. a coupling step comprising contacting a sulfonic acid of the formula

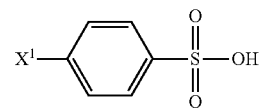

with an aryl compound of the formula

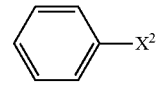

in the presence of a catalyst selected from the group consisting of aluminum oxide, antimony oxide, zirconium oxide, bismuth oxide, ferric oxide, stannic oxide, titanium oxide, titanium sulfate, zinc oxide, iodine, lithium iodide, and silica, wherein resulting water is removed during the coupling step; and
wherein trifluoroacetic anhydride is not present in the coupling step, and
wherein the process is free of dimethyl sulfate.
2. The process of claim 1, wherein $X^1$ and $X^2$ are Cl.
3. The process of claim 1, wherein the crude yield of the coupling step, as determined by the sulfone relative to the sulfonic acid, is about 60% to about 95%.

4. The process of claim 1, wherein the purified yield of the coupling step, as determined by the sulfone relative to the sulfonic acid, is about 50% to about 85%.

5. The process of claim 1, wherein the coupling step is initiated under anhydrous conditions.

6. The process of claim 1, wherein the coupling step is initiated with less than about 10 wt % water.

7. The process of claim 1, wherein the resulting water is removed continuously during the coupling step.

8. The process of claim 1, wherein the resulting water is removed by distillation.

9. The process of claim 1, wherein the concentration of water throughout the coupling step is less than about 10 wt % water.

10. The process of claim 1, wherein the coupling step is performed without a dehydrating reagent.

11. The process of claim 1, wherein the concentration of the catalyst relative to all components of the coupling step, when the coupling step is initiated, is about 0.7 wt % to about 1.1 wt %.

12. A process for preparing a sulfone of the formula

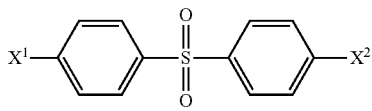

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl; the process comprising a. a coupling step comprising contacting a sulfonic acid of the formula

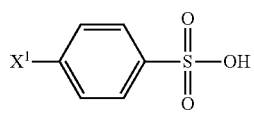

with an aryl compound of the formula

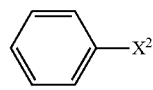

in the presence of a catalyst selected from the group consisting of aluminum oxide, antimony oxide, zirconium oxide, bismuth oxide, ferric oxide, stannic oxide, titanium oxide, titanium sulfate, zinc oxide, iodine, lithium iodide, and silica, wherein resulting water is removed during the coupling step, wherein the concentration of the catalyst relative to the sulfonic acid, when the coupling step is initiated, is about 0.01 equivalent to about 0.1 equivalent, wherein the process is free of dimethyl sulfate.

13. The process of claim 1, wherein the coupling step results in less than 20% of a 2,4' isomer of the formula

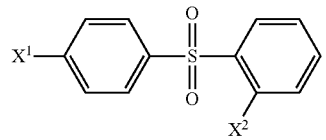

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, as determined by the 2,4' isomer relative to all sulfone products.

14. The process of claim 1, wherein the coupling step results in less than 20% of a 3,4' isomer of the formula

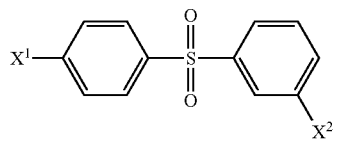

wherein $X^1$ and $X^2$ are independently H, halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, as determined by the 3,4' isomer relative to all sulfone products.

15. The process of claim 1, wherein the aryl compound is added to the sulfonic acid continuously at the same time that water is removed continuously from the sulfonic acid.

16. The process of claim 1, wherein the aryl compound is added to the sulfonic acid continuously at the same time that wet chlorobenzene is removed continuously from the sulfonic acid.

17. The process of claim 1, wherein the aryl compound is added at a flow rate of about 1.5 mL/min.

18. The process of claim 1, wherein the coupling step is performed at a pressure of about 30 psi to about 60 psi.

19. The process of claim 1, further comprising removing the aryl compound from the sulfone by distillation after the coupling step.

20. The process of claim 1, further comprising extracting the sulfone after the coupling step.

21. The process of claim 1, further comprising washing the sulfone with water.

22. The process of any claim 21, wherein the washing step results in the sulfone being substantial free of the sulfonic acid.

23. The process of claim 1, further comprising crystallizing the sulfone.

24. The process of claim 23, wherein the crystallizing step results in the sulfone having a purity of greater than about 99%.

25. The process of claim 1, further comprising a first step comprising contacting a reactant of the formula

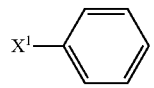

wherein $X^1$ is a H, halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, wherein each hydrogen atom in $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl is independently optionally substituted with a halogen, $C_1$-$C_6$ alkyl, $C_6$-$C_{10}$ aryl, —$C_1$-$C_6$ alkyl-($C_6$-$C_{10}$ aryl), —$C_1$-$C_6$ alkyl or —$C_6$-$C_{10}$ aryl, with sulfur trioxide to provide a first product mixture comprising the sulfonic acid.

26. The process of claim 25, wherein $X^1$ is Cl.

* * * * *